(12) United States Patent
Toler

(10) Patent No.: US 6,898,889 B1
(45) Date of Patent: May 31, 2005

(54) SHOOTER'S LENS DEVICE AND SELECTION THEREOF

(76) Inventor: Alan G. Toler, 3026 W. Cary St., Richmond, VA (US) 23221-3502

( * ) Notice: Subject to any disclaimer, the term of this patent is extended or adjusted under 35 U.S.C. 154(b) by 0 days.

(21) Appl. No.: 10/735,223

(22) Filed: Dec. 15, 2003

(51) Int. Cl.7 .................................................. F41G 1/46
(52) U.S. Cl. .............................. 42/111; 351/53; 351/57; 351/47
(58) Field of Search .............................. 42/90, 135, 111; 351/53, 57, 47

(56) References Cited

U.S. PATENT DOCUMENTS 1,547,406 A * 7/1925 Berling .......................... 351/53
5,153,619 A * 10/1992 Nix ................................ 351/57
5,604,548 A * 2/1997 Kanbar .......................... 351/56
5,726,731 A    3/1998 Toler

FOREIGN PATENT DOCUMENTS

JP          58-5714    *  1/1983 ................... 351/47

* cited by examiner

Primary Examiner—Stephen M. Johnson
(74) Attorney, Agent, or Firm—Norman Rainer

(57) ABSTRACT

An optical correcting system which enables a shooter to better see both the sights of his firearm and the target includes a series of lenses of sequentially incremental one quarter diopter optical power, a chart which facilitates selection of the appropriate lens, and a headband assembly which secures the selected lens in a manner to fit over the shooter's aiming eye. An identification code correlates the information on the chart with the chosen headband assembly.

11 Claims, 2 Drawing Sheets

INSTRUCTIONS:

In order to improve your aiming accuracy, select a lens based upon the table below. The selected lens is to be used over your best distance prescription lens in a safety-approved shooter's eyeglass. In employing the selected lens in such manner, concentrate on the front sight while aiming.

TABLE I

|  | pistol | pistol | rifle | rifle | rifle |
|---|---|---|---|---|---|
| TARGET DISTANCE (yards) | 0-50 | 51-100 | <200 | 300-600 | >600 |
| TARGET DIAMETER (inches) | 6 | 8 | 13 | 19-72 | 72 |
| AGE | | | | | |
| <35 | red | red | white | red | red |
| 36-45 | white | red | white | white | red |
| 46-55 | blue | white | blue | white | red |
| 55+ | blue | white | blue | white | white |

FOR STRONGER MAGNIFICATION IN ALL CATEGORIES, TRY YELLOW FIRST, THEN GREEN.

FIG. 1

SHOOTER'S LENS DEVICE AND SELECTION THEREOF

BACKGROUND OF THE INVENTION

1. Field of the Invention

This invention relates to the aiming of a shooting device having aiming sights, and more particularly concerns a lens system which enhances a shooter's ability to see his sights and intended target.

2. Description of the Prior Art

In the case of firearms such as rifles and pistols, aiming is generally achieved by visually aligning a rear sight and a front sight with an intended target. To achieve such alignment, the shooter's eye must attempt to focus on all three components, namely rear sight, front sight and target. Ideally, if all three components were clearly in focus in the shooter's eye, accurate aiming is achieved.

In reality however, it is impossible for the human eye to focus simultaneously on several linearly separated objects such as a rear sight, front sight and distant target. Furthermore, focusing difficulty increases with the shooter's age. Although eyeglasses can improve the shooter's ability to focus upon an object at a specific distance, it generally worsens the ability to focus at other distances. Accordingly, if a shooter, with or without glasses, is focusing upon a distant target, his vision of his rear sight is blurred. Conversely, if the same shooter focuses upon his rear sight, then the target becomes blurred.

Many shooters, in the course of aiming will cause their eye to focus repeatedly and sequentially between rear sight, front sight and target. Such action not only causes eye fatigue, but still falls short of the ideal situation where the sights and target are simultaneously in relatively clear focus.

Standard prescription eyeglasses lenses are generally powered to the quarter diopter, namely 0.25, 0.50, 0.75 and 1.00, etc. The tolerance to which said standard prescription lenses are ground is typically plus or minus an eighth diopter.

Although some of the shooter's visual problems could possibly be resolved by a trained optometrist who would examine the shooter at the target or hunting range, such examination would be expensive.

U.S. Pat. No. 5,726,731 to Toler discloses a system for enabling a shooter to select a specialized eyeglass lens which will improve his ability to see both the sights and target. However, the system involves some cost, or alternatively may involve a fee to an optometrist employing the system. Additional expense is incurred when the appropriate eyeglasses are made by an optometrist. Such cost may be significant if the specialized prescription eyeglasses further incorporate standard features of shooter's glasses such as shatter resistance, glare resistance and special tint for absorption of ultraviolet components of sunlight. Furthermore, the lens selection system of said patent may involve weeks of delay between the time the proper lens is ascertained and receipt of appropriate eyeglasses from the optometrist.

It is accordingly an object of this invention to provide a simple and rapid method for ascertaining an individual shooter's visual needs for focusing on the sights of his firearm and the intended target.

It is another object of the present invention to provide an inexpensive optical device whose characteristics are selected by the method of the foregoing object.

It is a further object of this invention to provide an optical device of the aforesaid nature which can be utilized in association with commonplace shooter's glasses.

These objects and other objects and advantages of the invention will be apparent from the following description.

SUMMARY OF THE INVENTION

The above and other beneficial objects and advantages are accomplished in accordance with the present invention by an optical correcting system for a shooter using a firearm having front and rear sights, said system comprising:

1) a lens selection chart incorporating selection criteria including the age of the shooter, distance and size of the target, and whether pistol or rifle, said criteria determining the optical power of a corrective lens for enabling the shooter to focus on both the sights and target, and identification code means associated with a selected corrective lens dictated by said chart, and 2) a headband assembly which secures said selected corrective lens in a manner to fit over the eye that the shooter uses for aiming, said headband assembly further having associated therewith said identification code means.

In preferred embodiments, the headband is elastic and of adjustable size, and further contains a removable eye patch positionable over the shooter's non-aiming eye. The selected lens is of sufficiently large diameter to fit over or behind a commonplace eyeglass frame.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing:

FIG. 1 is a plan view of a lens selector chart employed in the practice of the present invention.

DESCRIPTION OF THE PREFERRED EMBODIMENT

Referring now to FIG. 1, an embodiment of lens selection chart 10 is shown having instructional information 11 relative to the proper use of a selected lens. Table I of chart 10 presents selection criteria 12 which interactively considers the shooter's age, shooting distance, target size, and handgun versus rifle. The vertical columns in Table I present lens selections in terms of a selection identification code. In the preferred embodiment, the identification codes are the colors: red, white, blue, yellow and green. However, in alternative embodiments, other equivalent identification codes may be employed.

In one aspect of the present invention, it has been discovered that the lens in Table I which is designated "red" should have a diopter value of 0.25, the "white" coded lens should have a diopter value of 0.50, the "blue" coded lens should have a diopter value of 0.75, the "yellow" coded lens should have a diopter value of 1.00, and the "green" coded lens should have a diopter value of 1.25. Such discovery is based upon a careful study of shooters and the shooting parameters shown in Table I. It has been found, surprisingly, that essentially all shooting parameters can be resolved with just five specific corrective lenses.

Figure 2:
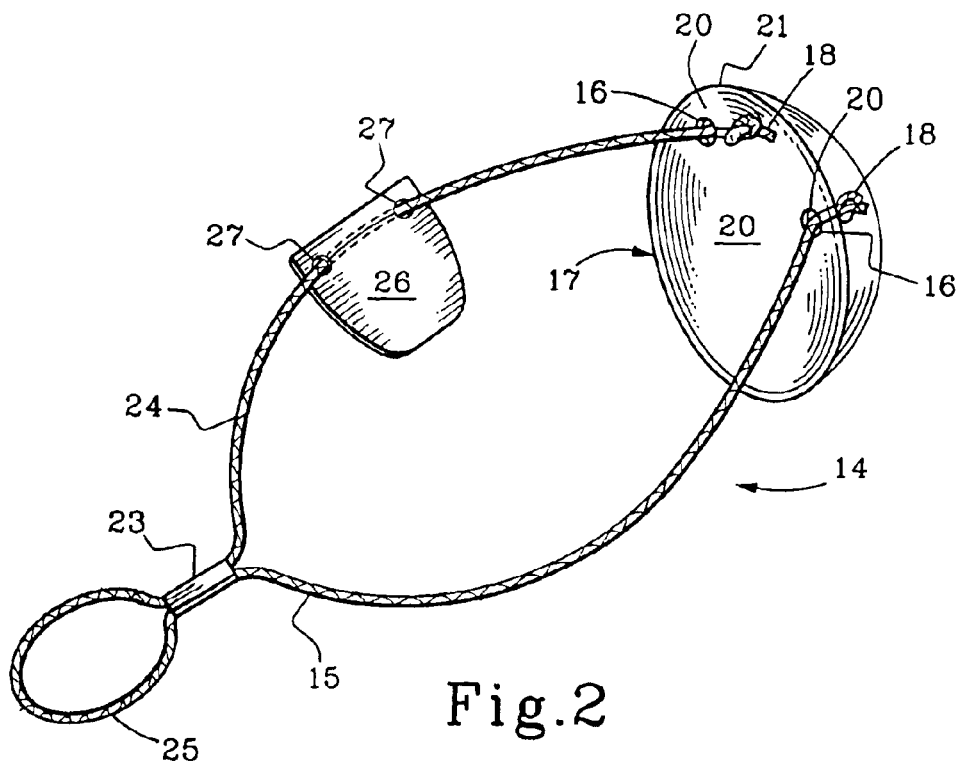
FIG. 2 is a perspective view of an embodiment of the headband assembly employed in the practice of this invention.
Figure 3:
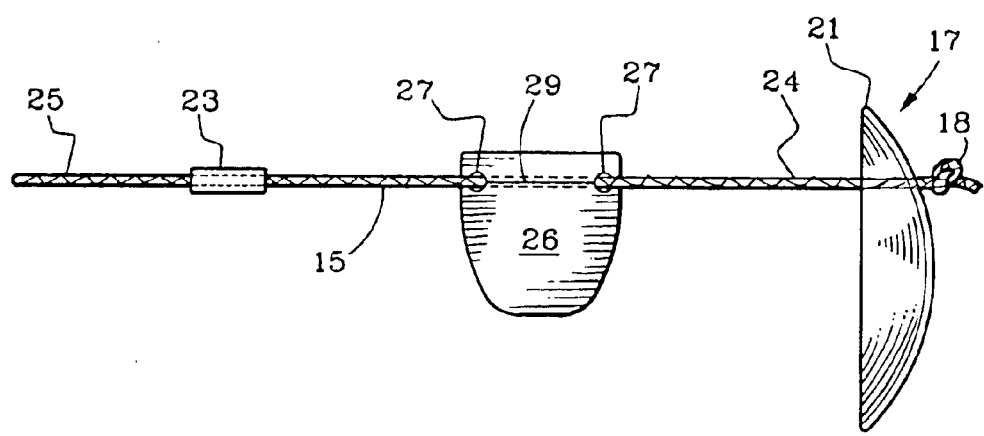
FIG. 3 is a side view of the headband assembly of FIG. 2.

Selection chart 10 is intended to be displayed in a store that sells shooting supplies. Associated with chart 10 are packaged headband assemblies 14, as shown in FIG. 2. In fact said chart and one or more headband assemblies are preferably packaged as a kit which can be selectively purchased by the shooter.

The exemplified embodiment of headband assembly 14 is comprised of a thin elastomeric band 15 extending between two extremities 20 which penetrate opposed holes 16 in the upper extremity 21 of lens 17, and are secured by knots 18 on the convex surface 19 of said lens. Band 15 is thereby disposed as a primary closed loop 24 which faces the concave surface 20 of said lens.

A snugging collar 23 may be mounted on said band in a manner to engage doubled lengths of said band. Collar 23 is slideable upon said doubled length with sufficiently strong frictional engagement to produce a secondary closed loop 25 which effectively adjusts the diameter of primary closed loop 24.

A flat opaque patch 26 may be disposed upon band 15 by way of opposed apertures 27 in patch 26, through which the band passes, thereby permitting sliding adjustment. A slit 29 extending between apertures 27 permits easy removal of the patch. The patch is intended to be optionally employed by shooters who cannot effectively aim with both eyes open, but do not want to close their non-aiming eye.

The manner of association of the lens and patch with the band is such that the lens and patch can be employed on either eye of the shooter. The circular diameter of lens 17 is sufficiently large, between 60 and 80 millimeters, so as to easily fit over the standard shooting glasses normally worn by the shooter. For reasons of safety, reduced weight, and reduced cost, the lens is preferably of plastic construction, and is intended to be used over safety eyeglasses. The lens may include bifocal characteristics.

In the exemplified embodiment of headband assembly 14, identification code means is incorporated into collar 23. For example, the color of the collar is consistent with the colors listed in Table I, thereby enabling the proper lens to be selected based upon the dictates of the Table. In alternative embodiments, the identification means may be a ribbon, tag, bead or marking on or coloration of the patch. The colored collar is an easily discernible feature in a packaged item on a store shelf.

By virtue of the aforesaid characteristics, the shooter's aiming ability can be easily, inexpensively and rapidly improved by the vision-correcting system of the present invention. Because he can select the lens himself, and purchase it immediately, he avoids the expense and long waiting time that would have been required if he sought the services of an optometrist to achieve the same end result.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

What is claimed is:

1. An optical correcting system for a shooter using a firearm having front and rear sights, said system comprising:
   a) a series of corrective lenses of sequentially incremental one quarter diopter optical power,
   b) a lens selection chart incorporating selection criteria including the age of the shooter, distance and size of the target, and whether pistol or rifle, said criteria determining the optical power of a corrective lens for enabling the shooter to focus on both the sights and target, and identification code means associated with a selected corrective lens dictated by said chart, and
   c) a headband assembly which secures said selected corrective lens in a manner to fit over the eye that the shooter uses for aiming, said headband assembly further having associated therewith said identification code means.

2. The optical correcting system of claim 1 wherein said headband assembly is comprised of an elastic band.

3. The optical correcting system of claim 1 wherein said lens is of sufficiently large diameter to fit over a commonplace eyeglass frame.

4. The optical correcting system of claim 1 wherein said identification code means is a series of color codes.

5. The optical correcting system of claim 2 wherein said lenses are comprised of a set of five lenses having magnification powers of 0.25, 0.50, 0.75, 1.00 and 1.25 diopters.

6. The optical correcting system of claim 5 wherein each lens has a convex forward surface, concave rear surface and upper extremity having two laterally separated holes.

7. The optical correcting system of claim 6 wherein said elastic band extends between two extremities which penetrate said holes and are secured by knots upon said convex surface, thereby forming a primary closed loop which faces said concave surface.

8. The optical correcting system of claim 7 further provided with a snugging collar mounted upon said band in a manner to engage doubled lengths of said band.

9. The optical correcting system of claim 8 wherein said collar is slideable upon said doubled length with sufficiently strong frictional force to produce a secondary closed loop which effectively adjusts the diameter of said primary closed loop.

10. The optical correcting system of claim 7 further having an opaque patch slideably disposed upon said band in a manner to permit positioning over the shooter's non-aiming eye.

11. The optical correcting system of claim 8 wherein said identification code means is incorporated into said collar.

* * * * *